United States Patent [19]

Stapp

[11] 4,164,615

[45] Aug. 14, 1979

[54] CONVERSION OF CONJUGATED DIENES TO DIACYLOXY OLEFINS

[75] Inventor: Paul R. Stapp, Bartlesville, Okla.

[73] Assignee: Phillips Petroleum Company, Bartlesville, Okla.

[21] Appl. No.: 827,632

[22] Filed: Aug. 25, 1977

[51] Int. Cl.$^2$ .............................................. C07C 67/05
[52] U.S. Cl. ................................. 560/246; 252/441; 260/410.6; 260/464; 260/465 D; 260/465.4; 560/1; 560/60; 560/83; 560/84; 560/85; 560/87; 560/89; 560/105; 560/106; 560/111; 560/112; 560/122; 560/125; 560/127; 560/192; 560/193; 560/197; 560/199; 560/228; 560/229; 560/230
[58] Field of Search ..................... 560/246, 1, 10, 112, 560/193, 199; 260/410.6, 464, 465 D, 465.4

[56] References Cited

U.S. PATENT DOCUMENTS

| 2,695,313 | 11/1954 | Toland | 260/530 |
|---|---|---|---|
| 2,870,196 | 1/1959 | Barnay | 260/485 |
| 2,903,480 | 9/1959 | Toland | 260/523 |
| 2,985,521 | 5/1961 | Herman | 44/57 |
| 3,119,874 | 1/1964 | Paszthory | 260/597 |
| 3,119,875 | 1/1964 | Steinmetz | 260/604 |
| 3,479,395 | 11/1969 | Huguet | 560/246 |
| 3,634,496 | 1/1972 | Kominami | 260/497 |
| 4,026,924 | 5/1977 | Stapp | 560/246 |

FOREIGN PATENT DOCUMENTS 1368505  9/1974  United Kingdom .

OTHER PUBLICATIONS

Suzuki, Ind. & Eng. Chem. Prod. Res. Dev., 10, pp. 179-183 (1973).
Hill, Chem,. Rev., 61, pp. 537-562 (1961).

*Primary Examiner*—Bernard Helfin
*Assistant Examiner*—Michael Shippen

[57] ABSTRACT

A catalyst comprising a titanium compound, an alkali metal ion, and a halide, is effective for the conversion of conjugated diolefins to diacyloxy olefins.

28 Claims, No Drawings

CONVERSION OF CONJUGATED DIENES TO DIACYLOXY OLEFINS

FIELD OF THE INVENTION

The invention pertains to the oxidation of conjugated dienes to diacyloxy olefins. In another aspect the invention pertains to a titanium catalyst system.

BACKGROUND OF THE INVENTION

Conjugated diolefins, such as butadiene, present an intriguing possible source of a variety of more valuable chemicals. Conjugated dienes, obtained from various sources such as the conversion of refinery streams obtainable in integrated refineries sometimes termed a petro complex, are relatively cheap chemicals. Conversion of such unsaturates potentially could provide routes to many other useful and valuable intermediates and end products. For example, 1,4-butanediol is a valuable intermediate used in the preparation of polybutylene terephthalate, an engineering type plastic.

BRIEF DESCRIPTION OF THE INVENTION

I have discovered that a catalyst system comprising a titanium compound, an alkali metal ion, and a halide, is effective for the conversion of conjugated diolefins to diacyloxy olefins. The resulting diacyloxy olefins are readily converted to the corresponding saturated diols, tetrahydro-furan or substituted tetrahydrofurans.

DETAILED DESCRIPTION OF THE INVENTION

Conjugated Diolefins

The conjugated diolefin can be either acyclic or cyclic, substituted or unsubstituted, and there does not presently appear to be any limitation on molecular size except convenience and availability.

The acyclic conjugated diolefins, preferably of 4 to 16 carbon atoms per molecule for convenience and availability, correspond to the general formula:

(I).

The cyclic conjugated diolefins, preferably of 5 to 16 carbon atoms per molecule for convenience and availability, correspond to the general formula:

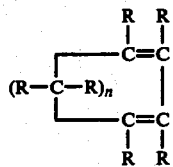
(II).

In each of the above formulas, each R is hydrogen, halogen, cyano, —COOR', or a hydrocarbyl radical of preferably not over 12 carbon atoms and which can be alkyl, aryl, cycloalkyl, or combinations thereof such as aralkyl, alkaryl, and the like. R' is hydrogen, or an alkyl radical of preferably not over 10 carbon atoms, or an aryl radical of preferably not over 10 carbon atoms. The n is an integer, preferably of 1 to 12.

Exemplary linear conjugated diolefins include: 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxycarbonyl-1,3-butadiene, 2-decyloxycarbonyl-1,3-butadiene, 2-phenoxycarbonyl-1,3-butadiene, 2-(1-naphthyloxy)carbonyl-1,3-butadiene, 2-benzyl-1,3-butadiene, 2-p-tolyl-1,3-butadiene, 2-chloro-3-methyl-1,3-butadiene, and the like, alone, or in admixture; or in admixture with cyclic diolefins; though preferably single species are employed.

Exemplary cyclic conjugated diolefins include 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 1,3-cyclohexadecadiene, 2-undecyl-1,3-cyclopentadiene, 2-methoxycarbonyl-1,3-cyclooctadiene, 2-decyloxycarbonyl-1,3-cyclopentadiene, 2-phenoxycarbonyl-1,3-cyclohexadiene, 2-(1-naphthyloxy)carbonyl-1,3-cyclopentadiene, 2-benzyl-1,3-cyclooctadiene, 2-p-tolyl-1,3-cyclohexadiene, and the like, alone or in admixture, though preferably single species are employed.

In a presently preferred embodiment, the conjugated diolefins employed in the process of my invention are the hydrocarbons, those which contain only carbon and hydrogen.

Catalyst System

The catalyst system employed for the conversion of conjugated diolefins to diacyloxy olefins in carboxylic acid media includes three components: a titanium compound, an alkali metal ion, and a halide, optionally with a dihalobutene. Presently preferably, the catalyst system consists essentially of these components.

The titanium compound component can be one or more of hydrocarbyl titanium compounds, hydrocarbyl titanium halides, or titanium halides, such that the halide is other than fluoride. These titanium compounds also can be represented by the (III) general formula $R''_q TiX_m$ in which m is 0 or an integer of 1 to 4; q is 0 or an integer of 1 to 4; X is chlorine, bromine, or iodine; and R'' is a hydrocarbyl radical, preferably having 1 to 18 carbon atoms, such as alkyl, aryl, alkaryl, aralkyl, cycloalkyl, cycloalkylaryl, or π-bonding unsaturated hydrocarbyl radicals such as π-allyl or π-cyclopentadienyl.

Exemplary titanium compounds include titanium trichloride, titanium tetrachloride, titanium tetrabromide, titanium tetraiodide, di-η-cyclopentadienyltitanium dichloride, di-η-indenyltitanium dichloride, titanium tribromide, dimethyltitanium dichloride, ethyltitanium trichloride, diphenyl(di-η-cyclopentadienyl)titanium, dimethyl(di-η-cyclopentadienyl)-titanium, decyltitanium trichloride, octadecyltitanium trichloride, p-tolyltitanium trichloride, benzyltitanium trichloride, cyclohexyltitanium trichloride, p-cyclohexylphenyltitanium trichloride, di-η-allyltitanium dichloride, and the like, alone, or in admixture.

It will be recognized by those skilled in the art that these titanium compounds cover a wide range of stability characteristics. For this reason and also because of availability considerations, the presently preferred titanium compounds for use in the process of my invention are the cyclopentadienyltitanium compounds and the binary titanium halides.

Any alkali metal compound can be used so long as it is suitable and effective and is sufficiently soluble in the media as to contribute the desired alkali metal ion. The alkali metal can be any one or more of lithium, sodium, potassium, rubidium, or cesium. Suitable alkali metal compounds include the halides, nitrates, carboxylates, oxides, and hydroxides.

Exemplary alkali metal compounds include lithium chloride, lithium bromide, lithium iodide, lithium acetate, lithium benzoate, lithium oxide, lithium octadecanoate, lithium nitrate, sodium chloride, sodium bromide, sodium acetate, sodium nitrate, potassium chloride, potassium acetate, potassium benzoate, potassium nitrate, rubidium chloride, rubidium bromide, rubidium acetate, rubidium nitrate, cesium chloride, cesium acetate, cesium oxide, cesium nitrate, and the like, and mixtures thereof.

The third component of my catalyst system is a source of halide ion, specifically chloride, bromide, iodide, or mixtures of these ions. The halide ion can be supplied, of course, at least in part, or all, by either the titanium compound, by the alkali metal compound, or both. Other halide ion sources can be employed provided that the cation portion of the halide ion containing compound is substantially inert under reaction conditions employed according to my invention.

Exemplary halide ion sources include the alkaline earth metal halides, such as magnesium chloride, calcium bromide, magnesium iodide, strontium bromide, barium chloride, and the like, as well as the appropriate already described titanium compounds and alkali metal compounds.

It is optional, though preferred, to further employ a dihalobutene, such as 1,4-dichloro-2-butene, or the corresponding dibromo or diiodo compounds, as a catalyst adjuvant. The dihalobutenes appear to serve as sources of halide ion and to promote the reaction rate of the oxidation reaction.

The amount of my catalyst system employed in the process of my invention can be expressed in terms of the mole percent of the titanium compound based on the amount of the conjugated diolefin charged to the reaction mixture. The ratios can range widely, so long as effective for the oxidation results desired. Presently considered exemplary is an amount of the titanium compound in the range of about 0.1 to 20, preferably about 1 to 10, mole percent relative to the conjugated diolefin.

The amounts of the alkali metal compound and of the halide ion employed in the porcess of my invention are conveniently based on the titanium compound. The ratios can range widely, so long as effective for the oxidation results desired. Presently considered exemplary is a molar ratio of alkali metal compound to titanium compound, and a molar ratio of halide ion to titanium compound, each in the range of about 0.1:1 to 20:1, preferably about 1:1 to 10:1.

Similarly, when employed, the amount of the dihalobutene catalyst adjuvant is based on the titanium compound. The ratios can range widely, so long as effective for the oxidation results desired. Presently considered exemplary is a molar ratio of the dihalobutene to the titanium compound in the range of about 0.1:1 to 10:1, preferably about 0.5:1 to 5:1.

Carboxylic Acid Media/Reactant

The term carboxylic acid media includes the use of mono- or dicarboxylic acids alone, or in admixture with each other, or with the anhydrides. The carboxylic acid employed in the process of my invention includes monocarboxylic acids, dicarboxylic acids, or both, preferably of up to 18 carbon atoms per molecule for availability and to be reasonably liquid under suggested reaction conditions, and most preferably in conjunction with an anhydride.

The monocarboxylic acids, preferably of 2 to 18 carbon atoms per molecule, can be characterized by the (IV) general formula R''' —COOH in which R''' is an alkyl, cycloalkyl, or aryl radical, and includes halogen, cyano, and —COOR' substituted derivatives thereof wherein up to four halogen, cyano, or —COOR' substituents can be present in the R''' group. R' is as previously defined.

The dicarboxylic acids, preferably of 2 to 18 carbon atoms per molecule, can be characterized by the (V) general formula R''''(COOH)$_2$ in which R'''' is a valence bond, or is an alkylene, cycloalkylene, or arylene radical, in which up to four halogen, cyano and —COOR' substituents can be present in the R'''' group. R' is previously defined.

Exemplary carboxylic acids include acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, oxalic acid, succinic acid, adipic acid, terephthalic acid, 2-bromobutanoic acid, ethyl hydrogen adipate, 4-chlorobenzoic acid, 4-cyclohexylbenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, and the like, alone, or in admixture.

It is optional, though presently preferred, to employ, as part of the reaction mixture, a carboxylic acid anhydride in addition to the carboxylic acid, preferably the corresponding carboxylic acid anhydride. The use of a carboxylic acid anhydride serves to simplify the purification and separation steps by reducing the amount of by-products which contain free hydroxy groups. Exemplary anhydrides include those corresponding to the described acids and need not be individually recited.

The presently preferred carboxylic acid is acetic acid, and presently preferred is a carboxylic acid media of acetic acid/acetic anhydride.

Reaction Conditions

The process of my invention is an oxidation reaction and as such is carried out in the presence of free oxygen. The amount of oxygen present is not believed to be critical, though it is recognized that an undesirably slow reaction will result if the concentration of oxygen is very low. Pure oxygen can be employed, or mixtures of oxygen with inert gases such as air can be employed as a convenient source of free oxygen for my process.

It is recognized that explosive conditions could be attained if the amount of oxygen added to the reaction system is not properly controlled. The process of my invention, as is true with many oxidation reactions, is highly exothermic and this aspect further dictates caution in adding oxygen to the reaction system. Because of these considerations, it is desirable to add the oxygen incrementally or continuously during the reaction to avoid reaching an explosive range of oxygen concentrations, and to allow better control of the temperature of the reaction. A reaction vessel with efficient mixing means thus is desirable to avoid build-up of potentially dangerous concentrations of free oxygen.

The reactions of my process can be carried out at any convenient temperature so long as the temperature is effective for the reactions, and not so high as to be unduly hazardous. Exemplary temperatures lie in the range of about 25° C. to 200° C., presently preferably about 70° C. to 150° C.

The process can be carried out under any suitable oxygen pressurization over a broad range, so long as sufficient oxygen is provided to be effective in the oxidation reactions, not cause unduly long times of reaction, and at the same time not be so high in concentration as to provide unduly hazardous conditions. An exemplary range of oxygen pressure is about 0.1 to 1,000, presently preferably about 5 to 200, psig of oxygen above autogenous pressure at the temperature employed.

The reaction time can range widely, as desired or convenient. The reaction time depends on the temperature, catalyst activity, and the oxygen pressure employed. An exemplary range is about 0.1 to 12 hours.

The reaction of my invention is carried out in contact with carboxylic acid media which provides the acyloxy and/or acyl moiety of the final product. Although some diacyloxy olefin product can be obtained using a wide range of ratios of carboxylic acid media to conjugated diolefin, it presently is apparent that the best yields can be obtained when the molar ratio of carboxylic acid media or reactant to conjugated diolefin reactant is at least about 2:1. In this connection, one mole of the corresponding carboxylic anhydride is equivalent to 2 moles of carboxylic acid. Ratios lower than about 1:1 should not be employed due to reduced yields, and ratios considerably higher than 2:1 can be employed, such as up to about 50:1 or higher, since the excess carboxylic acid media then serves as a reaction diluent.

The ratio of acid:anhydride, where the anhydride is employed, can range widely so long as effective. A suggested ratio is about 1:2 to 4:1, presently preferred about 2:1 by volume.

The process of my invention can be carried out in a batch or a continuous fashion, and in the liquid phase or in the gas phase. In a presently preferred embodiment, the process is carried out in the liquid phase. When conducted in the liquid phase, it is preferred that the carboxylic acid media employed in the process of my invention be normally liquid or at least liquid under the conditions employed for the reaction.

Product Recovery

Reaction mixtures obtained in the process of my invention can be readily treated for product recovery. The reaction mixture generally is vented to remove any unreacted oxygen and conjugated diolefin, and then distilled to remove remaining carboxylic acid media. The product remaining then can be treated, such as by distillation, to recover one or more fractions containing the desired diacyloxy olefin product. In many instances the catalyst can be recovered from the distillation residue, such as by evaporation of the residue to dryness, and recycled to the reaction zone as desired.

The diacyloxy olefins recovered from the product mixture include in many instances an amount of 1,2- or vicinal isomer which can be recycled to the reaction zone and thereby converted to the more desired 1,4-diacyloxy olefin. Of course, unreacted conjugated diolefin also can be recycled if desired.

Diacyloxy Olefins

Diacyloxy olefins produced according to the process of my invention can be represented by the following general formulas using reactants as indicated:

| Reactants | | Products |
|---|---|---|
| Carboxylic Acid Formula | Conjugated Diolefin Formula | Diacyloxy Olefin |
| (IV) | (I) | (VI) $\;\; R\!-\!\underset{\underset{\underset{R'''}{C=O}}{O}}{\overset{R}{C}}\!-\!C\!=\!C\!-\!\underset{\underset{\underset{R'''}{C=O}}{O}}{\overset{R}{C}}\!-\!R$ |
| (IV) | (II) | (VII) |

| Reactants | | Products |
|---|---|---|
| Carboxylic Acid Formula | Conjugated Diolefin Formula | Diacyloxy Olefin |
| (V) | (I) | (VIII) $$\begin{array}{c} R \quad\quad R \\ | \quad\quad | \\ R-C-C{=}C-C-R \\ | \quad | \quad | \quad | \\ O \quad R \quad R \quad O \\ | \quad\quad\quad\quad | \\ C{=}O \quad\quad C{=}O \\ | \quad\quad\quad\quad | \\ R'''' \quad\quad R'''' \\ | \quad\quad\quad\quad | \\ CO_2H \quad\quad CO_2H \end{array}$$ |
| (V) | (II) | (IX). 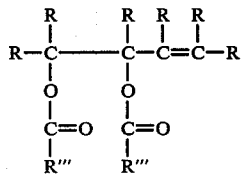 |

The product formulas VI, VII, VIII, and IX depict only the predominant diacyloxy olefin product obtained in the reactions indicated. These products generally are accompanied by relatively smaller amounts of isomeric diacyloxy olefins. For example, using general formula VI as an illustration, the isomeric product can be represented by the general formula:

$$\begin{array}{c} R \quad\quad R \quad R \quad R \\ | \quad\quad | \quad | \quad | \\ R-C{-\!-\!-}C-C{=}C-R \\ | \quad\quad\quad | \\ O \quad\quad\quad O \\ | \quad\quad\quad | \\ C{=}O \quad\quad C{=}O \\ | \quad\quad\quad | \\ R''' \quad\quad R''' \end{array} \quad (X).$$

Examples of diacyloxy olefins of product formula VI include: 1,4-diacetoxy-2-butene, 1,4-diacetoxy-2-hexadecene, 1,4-dioctanoyloxy-2-chloro-3-methyl-2-butene, 1,4-di(trichloroacetoxy)-2-cyano-2-butene, and 1,4-dibenzoyloxy-2-ethoxycarbonyl-2-butene.

Examples of diacyloxy olefins of product formula VII include: 3,5-diacetoxycyclopentene, 3,6-di(-chloroacetoxy)cyclohexene, 3,8-di(cyanoacetoxy)-cyclooctene, 3,12-diacetoxycyclododecene, 3,8-butanoyloxy-4,5,6,7-tetrabromocyclooctene and 3,5-di(trichloroacetoxy)hexachlorocyclopentene.

Examples of diacyloxy olefins of product formula VIII include: 1,4-butene-2-diyl di(hydrogen oxalate), 1,4-butene-2-diyl di(hydrogen adipate), 2-chloro-3-methyl-1,4-butene-2-diyl di(hydrogen succinate), and 1,4-hexadecene-2-diyl di(hydrogen terephthalate).

Examples of diacyloxy olefins of product formula IX include: 3,5-cyclopentendiyl di(hydrogen oxalate), 3,8-cyclooctenediyl di(hydrogen succinate), 3,6-cyclohexenedlyl di(hydrogen adipate) and 3,12-cyclododecenediyl di(hydrogen terephthalate).

EXAMPLES

The following examples are intended to assist one skilled in the art to a further understanding of the invention. Particular species, amounts, and relationships, are intended to be exemplary and not limitative of the scope of my invention.

EXAMPLE I

A 250 ml Fisher-Porter aerosol compatibility bottle equipped with a magnetic stirrer was charged with 2.5 grams (10 mmoles) of di-η-cyclopentadienyltitanium dichloride, 2.3 grams (10.7 mmoles) of 1,4-dibromo-2-butene, 6.5 grams (75 mmoles) of lithium bromide, 50 ml( (873 mmoles) of acetic acid, and 25 ml (265 mmole) of acetic anhydride. To this mixture was charged 11.5 grams (212.9 mmoles) of 1,3-butadiene in the vapor phase. The reactor was placed in an oil bath, pressured to 30 psig with oxygen and heated to 140° C. About 1 hour was required to reach the desired reaction temperature of 140° C. after which the reaction was continued for 4.5 hours. During the reaction period the reactor was pressured intermittently to 130 psig with oxygen at about 20 to 40 minute intervals. At the end of the reaction period the reactor was cooled, vented, and weighed. A weight gain of 5.1 grams was obtained during the oxidation reaction reflecting the uptake of oxygen.

The reaction mixture was transferred to a distillation flask and then distilled through an 18 inch Vigreux column. Two fractions were collected. Fraction 1 boiled from 47 to 56° C. at 50 mm mercury pressure and weighed 21.3 grams. Based on previous experience with similar oxidation reaction mixtures. Fraction 1 consisted essentially of acetic acid and acetic anydride.

Fraction 2 was analyzed by gas-liquid phase chromotography which indicated the presence of 2.30 grams (13.4 mmoles) of 1,2-diacetoxy-3-butene, 2.59 grams (15.1 mmoles) of cis-1,4-diacetoxy-2-butene, and 13.83 grams (80.4 mmoles) of trans-1,4-diacetoxy-2-butene, for a total of 108.9 mmoles of diacetoxy butenes. The yield of diacetoxy butenes based on the butadiene charged thus was 51.2 percent.

The results of this run demonstrate the effectiveness of my process for the oxidation of conjugated diolefins to diacyloxy olefins with my catalyst system.

EXAMPLE II

Utilizing the same type of apparatus and procedure as described in Example I above, another run was carried in which the catalyst system utilized was 3.0 grams (10 mmoles) of di-$\eta$-cyclopentadienylzirconium dichloride, 2.3 grams (10.7 mmoles) of 1,4-dibromo-2-butene, and 6.5 grams (75 mmoles) of lithium bromide, in a carboxylic acid media of 50 ml of acetic acid and 25 ml of acetic anhydride. To this mixture was charged 11.0 grams (203.7 mmoles) of butadiene in the vapor phase. The bottle reactor was placed in an oil bath, pressured to 30 psig with oxygen, and heated to 140° C. About 1.5 hours were required to reach the desired reaction temperature of 140° C. after which the reaction was continued for 5 hours with intermittent repressuring of the reactor to 120 psig with oxygen as previously described in Example I. At the end of the reaction period the bottle was cooled, vented, and weighed. A weight gain of 6.0 grams was obtained during the oxidation reaction.

The viscous black reactor mixture was transferred to a distillation flask and distilled through an 18 Vigreaux column. Only one fraction was obtained overhead in the distillation. The fraction boiled from 45° to 46° C. at 50 mm mercury pressure, weighed 117.6 grams, and was evidently the acetic acid and acetic anhydride as had been obtained in previous runs including that of Example I above. After the removal of this acetic acid/acetic anhydride fraction, essentially no liquid residue remained in the distillation flask which now contained a black tarry material. The nature of the reaction products obtained with the zirconium-based catalyst system was not analyzed further.

The results of this run demonstrate that under essentially the same reaction condition as in Example I, a closely related compound, the zirconium analog of the di-$\eta$-cyclopentadienyltitanium dichloride, was ineffective for the production of diacyloxy olefins by the oxidation of a conjugated diolefin.

EXAMPLE III

In essentially the same manner as that described for the runs of Examples I and II above, another run was carried out in which the 250 ml Fisher-Porter aerosol compatibility bottle reactor equipped with a magnetic stirrer was charged with 2.5 grams (10.7 mmoles) of 1,4-dibromo-2-butene, 6.5 grams (75 mmoles) of lithium bromide, 2.0 grams (10 mmoles) of di-$\eta$-cyclopentadienyliron (ferrocene), 50 ml of acetic acid and 25 ml of acetic anhydride. To this mixture was charged 12.2 grams (226.0 mmoles) of butadiene in the vapor phase. The bottle reactor was placed in an oil bath, pressured to 30 psig with oxygen and heated to 140° C. About 2 hours were required to reach the desired reaction temperature of 140° C. after which the reaction was continued for 5 hours with intermittent repressuring of the reactor with oxygen to 130 psig at about 20 to 30 minute intervals. After the reaction period, the bottle was cooled, vented, and weighed. A weight gain of 6.5 grams was obtained during the oxidation reaction.

The reaction mixture was transferred to a distillation flask and distilled through an 18 inch Vigreux column. Fraction 1 obtained during the distillation boiled from 42° to 49° C. at 50 mm mercury pressures and weighed 120.1 grams, while fraction 2 boiling at 34° to 92° C. at 5 mm mercury pressure weighed 6.8 grams. As in the previous runs, fraction 1 was composed of essentially acetic acid and acetic anhydride.

Gas-liquid phase chromatography analysis of Fraction 2 indicated the presence of 4.06 grams (23.6 mmoles) of 1,2-diacetoxy-3-butene and 1.00 gram (5.8 mmoles) of a mixture of cis and trans-1,4-diacetoxy-2-butene, for a total yield of 29.4 mmoles of diacetoxy butenes or a 13 percent yield of diacetoxy butenes based on butadiene charged.

The results of this run demonstrate that the use of an iron component as a catalyst component in the oxidation was much inferior to the titanium compound in the production of diacyloxy olefins in the oxidation of a conjugated diene tin carboxylic acid media.

EXAMPLE IV

Another control run was carried out utilizing esentially the same procedures as described in Example I above, but with the use of a titanate ester as the titanium component of the catalyst system, specifically, tetrabutyl titanate (10 mmoles). This run also utilized 4.6 grams (21.5 mmoles) of 1,4-dibromo-2-butene rather than the 2.3 g amount used in Example I. There was observed very little oxygen uptake during the run. This indicated that a very slow reaction, if any, had occurred under conditions utilized. The reaction mixture obtained was not further analyzed. The results of this run demonstrate that a titanate ester compound was not a suitable titanium component in my catalyst system for the oxidation of conjugated diolefins to diacyloxy olefins.

Conversion of Diacyloxy Olefins To Diols

The diacyloxy olefins can be converted to diols by several known methods. For example, the diacyloxy olefins can be hydrolyzed under basic or acidic aqueous conditions to give olefinic diols which then can be hydrogenated to remove the olefinic unsaturation and thus provide other diols. Alternatively, the diacyloxy olefins can be hydrogenated first to remove olefinic unsaturation and then hydrolyzed to provide diols.

Utility

The diols are useful for conversion to polyesters or polyurethanes, and as solvents or humectants, or can be converted to the corresponding tetrahydrofuran or substituted tetrahydrofurans. Tetrahydrofuran itself has wide utility as a solvent, and as a randomizing agent in preparation of copolymers. The substituted tetrahydrofurans are useful for solvents and as intermediates in the preparation of diamines or dicarboxylic acids for polyamide preparation.

The disclosure, including data, has illustrated the value and effectiveness of my invention. The examples, the knowledge and background of the field of the invention and of general principles of chemistry and other applicable sciences, have formed the bases to which the broad descriptions of the invention, including the ranges of conditions and generic groups of operant components have been developed and have formed the bases for my claims here appended.

I claim:
1. A process for the production of diacyloxy olefins from conjugated diolefins which comprises:
   reacting at least one conjugated diolefin with oxygen and a carboxylic acid reactant media employing a catalyst system consisting essentially of (A) a titanium compound, (B) an alkali metal compound, and (C) a halide-source, and optionally (D) a dihalobutene adjuvant;

and wherein said conjugated diolefin is selected from substituted or unsubstituted diolefins, and where substituted the substituents thereof are selected from halogen, cyano, —COOR', or hydrocarbyl, where R' is hydrogen, alkyl, or aryl;

wherein said carboxylic acid reactant media is selected from the group consisting of aliphatic and aromatic mono- and dicarboxylic acids and mixtures thereof with acid anhydrides, of 2 to 18 carbon atoms per molecule;

said (A) titanium compound is a hydrocarbyl titanium compound, hydrocarbyl titanium halide, titanium halide, or mixture;

said (B) alkali metal compound is at least one halide, nitrate, carboxylate, oxide, or hydroxide of lithium, sodium, potassium, rubidium, or cesium;

and said (C) halide-source is a said (A) or (B) where said (A) or (B) is the halide, or alkaline earth metal halide, or mixture, wherein the halide is chloride, bromide, iodide, or mixture.

2. The process of claim 1 wherein said conjugated diolefin is an acyclic conjugated diolefin of 4 to 16 carbon atoms per molecule.

3. The process according to claim 2 wherein said acyclic conjugated diolefin is 1,3-butadiene, 2-methyl-1,3-butadiene, 2-chloro-1,3-butadiene, 2-ethyl-1,3-butadiene, 2-cyano-1,3-butadiene, 2-methylene-3-butenoic acid, 2,4-pentadienenitrile, 1,3-hexadecadiene, 2-methoxycarbonyl-1,3-butadiene, 2-decyloxycarbonyl-1,3-butadiene, 2-phenoxycarbonyl-1,3-butadiene, 2-(1-naphthloxy)carbonyl-1,3-butadiene, 2-benzyl-1,3-butadiene, 2-p-tolyl-1,3-butadiene, or 2-chloro-3-methyl-1,3-butadiene.

4. The process of claim 1 wherein said conjugated diolefin is a cyclic conjugated diolefin of 5 to 16 carbon atoms per molecule.

5. The process according to claim 4 wherein said cyclic conjugated diolefin is 1,3-cyclohexadiene, 1,3-cyclooctadiene, 1,3-cyclododecadiene, 5-methyl-1,3-cyclohexadiene, 2,4-cyclohexadiene-1,2-dicarboxylic acid, octafluoro-1,3-cyclohexadiene, hexachlorocyclopentadiene, 5,6,7,8-tetrabromo-1,3-cyclooctadiene, 1,3-cyclohexadecadiene, 2-undecyl-1,3-cyclopentadiene, 2-methoxycarbonyl-1,3-cyclooctadiene, 2-decyloxycarbonyl-1,3-cyclopentadiene, 2-phenoxycarbonyl-1,3-cyclohexadiene, 2-(1-naphthyloxy)carbonyl-1,3-cyclopentadiene, 2-benzyl-1,3-cyclooctadiene, or 2-p-tolyl-1,3-cyclohexadiene.

6. The process of claim 1 wherein said halide-source is substantially supplied by said (A) alkali metalcompound, said (B) titanium compound, or both.

7. The process of claim 1 wherein said halide-source is at least in part provided by at least one of an alkali metal halide or alkaline earth metal halide.

8. The process of claim 1 wherein said carboxylic acid reactant media monocarboxylic acid is represented by R''' — COOH; and said dicarboxylic acid is represented by R''''(COOH)$_2$;

wherein R''' is selected from the group consisting of alkyl, cycloalkyl, and aryl radicals, and halogen, cyano, and —COOR' substituted derivatives thereof wherein up to four of said halogen, cyano, or —COOR' substituents can be present in said R''' radical, R'''' is selected from the group consisting of a valence bond and alkylene, cycloalkylene, and arylene radicals, and halogen, cyano, and —COOR' substituted derivatives thereof wherein up to four of said halogen, cyano, or —COOR' substituents can be present in said R'''' radical; and wherein R' of a said substituted diolefin where other than hydrogen contains up to 10 carbon atoms.

9. The process of claim 8 wherein said carboxylic acid reactant media comprises said monocarboxylic acid, optionally with an anhydride, selected from the group consisting of acetic acid, propanoic acid, butanoic acid, pentanoic acid, hexanoic acid, octanoic acid, dodecanoic acid, octadecanoic acid, cyclopentanecarboxylic acid, cyclohexanecarboxylic acid, benzoic acid, chloroacetic acid, cyanoacetic acid, trichloroacetic acid, 2-bromododecanoic acid, 2-ethylhexanoic acid, adipic acid, 2-bromobutanoic acid, ethyl hydrogen adipate, 4-chlorobenzoic acid, 4-cyclohexylbenzoic acid, 2,3,4,5-tetrachlorobenzoic acid, ethyl hydrogen-o-phthalate, 4,6,8,10-tetracyanoundecanoic acid, 4,6,8,10-tetramethoxycarbonylundecanoic acid, 4-decyloxycarbonylcyclohexanecarboxylic acid, and mixtures.

10. The process of claim 8 wherein said carboxylic acid reactant media comprises said dicarboxylic acid, optionally with the anhydride, selected from the group consisting of oxalic acid, succinic acid, terephthalic acid, tetrabromo-1,4-benzenedicarboxylic acid, tetracyano-1,4-benzenedicarboxylic acid, tetramethoxycarbonyl-1,4-benzenedicarboxylic acid, 2-decyloxycarbonylhexanedioic acid, and mixtures.

11. The process of claim 8 employing said titanium compound in the range of about 0.1 to 20 mole percent relative to said conjugated diolefin, and each of said halide of said halide-source and said alkali metal compound is in the range of about 0.1 to 20 moles per mole of said titanium compound, and said dihalobutene where present is employed in a molar ratio of about 0.1:1 to 10:1 dihalobutene:titanium compound.

12. The process of claim 11 employing about 1 to 10 mole percent of said titanium compound, and about 1:1 to 10:1 ratio of said alkali metal compound and of said halide-source based on halide.

13. The process of claim 11 employing a contacting temperature in the range of about 25° to about 200° C. at an oxygen pressure in the range of 0.1 to 1000 psig above autogenous pressure at the temperature employed.

14. The process of claim 13 wherein said temperature is in the range of about 70° C. to 150° C., and said oxygen pressure is in the range of about 5 to 200 psig above autogenous.

15. The process of claim 14 employing said carboxylic acid anhydride corresponding to the carboxylic acid employed.

16. The process of claim 15 wherein said reaction is conducted in the liquid phase.

17. The process according to claim 11 wherein said titanium compound is represented by the formula R''$_q$TiX$_m$ wherein m is 0 or an integer of 1 to 4, q is 0 or an integer of 1 to 4, X is chlorine, bromine, or iodine, and R'' is a hydrocarbyl radical of 1 to 18 carbon atoms.

18. The process according to claim 17 wherein said titanium compound is selected from the group consisting of titanium trichloride, titanium tetrachloride, titanium tetrabromide, titanium tetraiodide, di-$\eta$-cyclopentadienyltitanium dichloride, di-$\eta$-indenyltitanium dichloride, titanium tribromide, dimethyltitanium dichloride, ethyltitanium trichloride, diphenyl(di-$\eta$-cyclopentadienyl)titanium, dimethyl(di-$\eta$-cyclopentadienyl)- titanium, decyltitanium trichloride, octadecyltitanium trichloride, p-tolyltitanium trichloride, benzyltitanium trichloride, cyclohexyltitanium trichloride, p-cyclohexylphenyltitanium trichloride, di-η-allyltitanium dichloride, and mixtures.

19. The process according to claim 17 wherein R" is selected from π-bonding unsaturated hydrocarbyl radicals.

20. The process according to claim 18 wherein said alkali metal compound is selected from the group consisting of lithium chloride, lithium bromide, lithium iodide, lithium acetate, lithium benzoate, lithium oxide, lithium octadecanoate, lithium nitrate, sodium chloride, sodium bromide, sodium acetate, sodium nitrate, potassium chloride, potassium acetate, potassium benzoate, potassium nitrate, rubidium chloride, rubidium bromide, rubidium acetate, rubidium nitrate, cesium chloride, cesium acetate, cesium oxide, cesium nitrate, and mixtures.

21. The process according to claim 19 wherein said conjugated diolefin is an acyclic hydrocarbon diolefin, and said carboxylic acid reactant media is a mixture of acetic acid and acetic anhydride.

22. The process according to claim 21 wherein said titanium compound is di-η-cyclopentadienyltitanium dichloride, said alkali metal compound is a lithium compound, said conjugated diolefin is 1,3-butadiene, said halide of said halide-source is chloride and bromide, said dihalobutene is employed and is 1,4-dibromo-2-butene, said carboxylic acid reactant media comprises acetic acid and acetic anhydride, and the resulting product mixture comprises 1,2-diacetoxy-3-butene, cis-1,4-diacetoxy-2-butene, and a trans-1,4-diacetoxy-2-butene.

23. The process of claim 8 wherein said diacycloxy diolefins are represented by

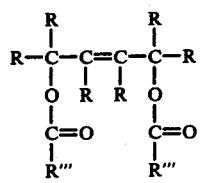

(VI)

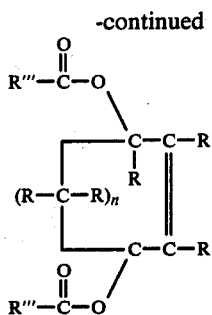

(VII)

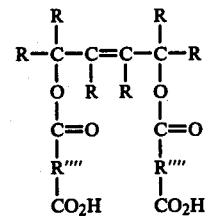

(VIII)

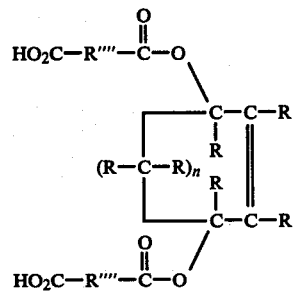

(IX).

24. The process according to claim 23 wherein said diacyloxy olefins are recovered from the resulting reaction product mixture, and any 1,2 or vicinal isomers are recycled to the reaction zone for further conversion to 1,4-diacyloxy olefin.

25. The process of claim 23 wherein the products comprise 1,4-diacetoxy-2-butene, 1,4-diacetoxy-2-hexadecene, 1,4-dioctanoyloxy2-chloro-3-methyl-2-butene, 1,4-di(trichloroacetoxy)-2-cyano-2-butene, or 1,4-dibenzoyloxy-2-ethoxycarbonyl-2-butene.

26. The process of claim 23 wherein the products comprise 3,5-diacetoxycyclopentene, 3,6-di(chloroacetoxy)cyclohexene, 3,8-di(cyanoacetoxy)cyclooctene, 3,12-diacetoxycyclododecene, 3,8-butanoyloxy-4,5,6,7-tetrabromocyclooctene, or 3,5-di(trichloroacetoxy)hexachlorocyclopentene.

27. The process of claim 23 wherein the products comprise 1,4-butene-2-diyl di(hydrogen oxalate), 1,4-butene-2-diyl di(hydrogen adipate), 2-chloro-3-methyl-1,4-butene-2-diyl di(hydrogen succinate), or 1,4-hexadecene-2-diyl di(hydrogen terephthalate).

28. The process of claim 23 wherein the products comprise 3,5-cyclopentenediyl di(hydrogen oxalate), 3,8-cyclooctenediyl di(hydrogen succinate), 3,6-cyclohexenediyl di(hydrogen adipate) or 3,12-cyclododecenediyl di(hydrogen terephthalate).

* * * * *

UNITED STATES PATENT AND TRADEMARK OFFICE
CERTIFICATE OF CORRECTION

PATENT NO. : 4,164,615
DATED : August 14, 1979
INVENTOR(S) : Paul R. Stapp

It is certified that error appears in the above-identified patent and that said Letters Patent are hereby corrected as shown below:

Claim 23, column 14, line 9 of patent - in (VII) the "R" is left off above the "C". Formula should be:

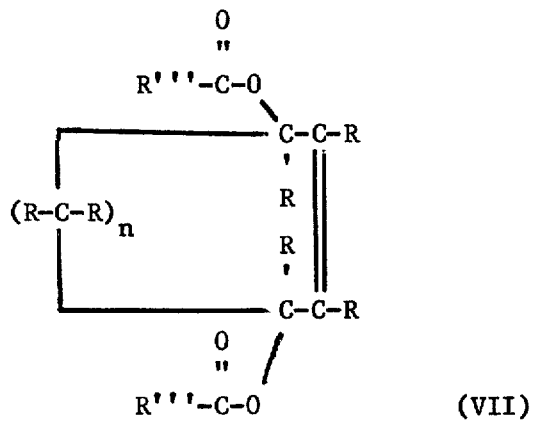

(VII)

Signed and Sealed this

Thirteenth Day of November 1979

[SEAL]

Attest:

RUTH C. MASON
Attesting Officer

LUTRELLE F. PARKER
Acting Commissioner of Patents and Trademarks